(12) United States Patent
Abbitt et al.

(10) Patent No.: US 7,897,746 B2
(45) Date of Patent: *Mar. 1, 2011

(54) PERICARP-PREFERRED PROMOTER FROM MAIZE LIPID TRANSFER PROTEIN GENE

(75) Inventors: Shane Abbitt, Ankeny, IA (US); Ramesh Nair, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 52 days.

This patent is subject to a terminal disclaimer.

(21) Appl. No.: 12/437,968

(22) Filed: May 8, 2009

(65) Prior Publication Data

US 2010/0275323 A1   Oct. 28, 2010

Related U.S. Application Data

(63) Continuation of application No. 11/408,223, filed on Apr. 20, 2006, now Pat. No. 7,550,579.

(60) Provisional application No. 60/676,616, filed on Apr. 29, 2005.

(51) Int. Cl.
C07H 21/04 (2006.01)
C12N 15/82 (2006.01)
A01H 5/00 (2006.01)

(52) U.S. Cl. ........ 536/24.1; 800/287; 800/278; 800/295; 800/298; 435/320.1

(58) Field of Classification Search .................. None
See application file for complete search history.

(56) References Cited

U.S. PATENT DOCUMENTS

| | | | |
|---|---|---|---|
| 5,525,716 | A | 6/1996 | Olsen et al. |
| 6,013,862 | A | 1/2000 | Simmonds et al. |
| 6,031,152 | A | 2/2000 | Olsen et al. |
| 6,326,528 | B1 | 12/2001 | Simmonds et al. |
| 6,429,357 | B1 | 8/2002 | McElroy |
| 6,939,958 | B1 | 9/2005 | Simmonds et al. |
| 2002/0069433 | A1 | 6/2002 | Schmidt et al. |
| 2003/0068791 | A1 | 4/2003 | Milasnikov et al. |
| 2004/0078851 | A1 | 4/2004 | Huang et al. |
| 2004/0103452 | A1 | 5/2004 | Russinova et al. |

FOREIGN PATENT DOCUMENTS

| | | |
|---|---|---|
| EP | 076623 A1 | 12/1996 |
| WO | WO9523230 A1 | 8/1995 |
| WO | WO9617945 A1 | 6/1996 |
| WO | WO9743427 A1 | 11/1997 |
| WO | WO9953067 A2 | 10/1999 |
| WO | WO0012733 A1 | 3/2000 |
| WO | WO0014237 A2 | 3/2000 |
| WO | WO0024024 A1 | 4/2000 |
| WO | WO0024914 A2 | 5/2000 |
| WO | WO0037488 A2 | 6/2000 |
| WO | WO0060089 A1 | 10/2000 |
| WO | WO0153306 A2 | 7/2001 |
| WO | WO0236635 A2 | 5/2002 |
| WO | WO02064750 A2 | 8/2002 |
| WO | WO02083912 A2 | 10/2002 |
| WO | WO03020937 A2 | 3/2003 |
| WO | WO03104465 A1 | 12/2003 |
| WO | WO2004035790 A1 | 4/2004 |
| WO | WO2004035798 A2 | 4/2004 |

OTHER PUBLICATIONS

Whitelaw et al. PUJEW62TD ZM_0.6_1.0_KB *Zea mays* genomic clone ZMBTa0652L03, genomic survey sequence. (2003) GenBank Accession CG194902; pp. 1-2.*
EMBL Jun. 20, 2003 "OGWEK34TH ZM_0.7 1.5kb *Zea mays* genomic clone ZMMBMa0559F19 genomic survey sequence" XP002410075; EBI accession No. EM_GSS:CC673046, Database Accession No. CC673046.
EMBL Aug. 25, 2003 "PUJEW49TB AM_0.6 kb *Zea mays* genomic clone ZMMBTa0652J01, genomic survey sequence" XP002410076, EBI accession No. EB_GSS:CG149831 Database accession No. CG149831.
Cocciolone et al. "Hierarchial patterns of transgene expression indicate involvement of developmental mechanisms in the regulation of the maize PL-rr promoter" Genetics, vol. 156, No. 2:839-846 (2000).
Federico et al. "The complex developmental expression of a novel stress-responsive barley Ltp gene is determined by a shortened promoter sequence" Plant Molecular Biology, vol. 57, No. 1: 35-51 (2005).
EMBL Aug. 25, 2003 "PUJEW62TD ZM_0.6 1kb *Zea mays* genomic clones ZMMBTa652I03 genomic survey sequence" XP002410077, EBI accession No. EB_GSS:CG19402 Database accession No. CG194902.
EMBL May 21, 2003 "PUHSS53TB ZM_0.6 1.0kb *Zea mays* genomic clone ZMMBTa525J09, DNA sequence" XP002417511, accession No. EB_PRO:CC442980.
Skriver et al. (1992) Plant Mol. Biol. 18:585-589. Federico et al. "A barley promoter for targeting transgene-mediated diseease resistance" (2002) Abstract. XII Plant and Animal Genome Conference proceedings p. 97 http://www.dfrc.ars.usda.gove/ccru/ronlab/ansku.html.
Opsahl-Sorteberg et al. "Identification of a 49-bp fragment of the HvLTP2 promoter directing aleurone cell specific expression" Gene 341 (2004) 49-58.
Konowicz et al. "Regulation of the osmotin gene promoter" The Plant Cell vol. 4, 513-524, May 1992 American Society of Plant Physiologists.
Chopra et al. "Alleles of the maize P gene with distinct tissue specificities encode Myb-homologous proteins with C-terminal replacements" The Plant Cell, vol. 8, 1149-1158, Jul. 1996, American Society of Plant Physiologists.
Wu et al. Plant J. Aug. 23, 2000(30 415-21.
Whitelaw et al. GenBank Accession CG194902, published Aug. 21, 2003, pp. 1-2.

(Continued)

*Primary Examiner* — Cathy Kingdon Worley
(74) *Attorney, Agent, or Firm* — Patricia A. Sweeney

(57) ABSTRACT

The present invention provides compositions and methods for regulating expression of heterologous nucleotide sequences in a plant. Compositions are novel nucleotide sequences for a pericarp-preferred promoter and terminator isolated from the maize lipid transfer protein 1 coding region. A method for expressing a heterologous nucleotide sequence in a plant using the regulatory sequences disclosed herein is provided. The method comprises transforming a plant cell to comprise a heterologous nucleotide sequence operably linked to one or more of the regulatory sequences of the present invention and regenerating a stably transformed plant from the transformed plant cell.

5 Claims, 5 Drawing Sheets

OTHER PUBLICATIONS

Maiti et al. "Promoter/leader deletion analysis and plant expression vectors with the figwort mosaic virus (FMV) full length transcript (FLt) promoter containing single or double enhancer domains" (1997) Transgenic Research; vol. 6, pp. 143-156.

Doelling et al. "The minimal ribosomal RNA gene promoter of *Arabidopsis thaliana* includes a critical element at the transcription initiation site" (1995) the Plant Journal; vol. 8, pp. 683-692.

Benfey et al. "The Cauliflower Mosaic virus 35S promoter: combinatorial regulation of transcription in plants" (1990) Science; vol. 250, pp. 959-966.

Kim et al. "A 20 nucleotide upstream element is essential for the nopaline synthase (nos) promoter activity" (1994) PMB; vol. 24, pp. 105-117.

Frederico et al. "A barkey promoter for targeting transgene-mediated disease resistance" (2003) Abstract XII Plant and Animal Genome Conference Proceedings p. 97 http://www.dfrc.usda.gove/ccru/ronlab/ansku.html.

Skadsen et al. "Development of tissue-specific gene promoters for targeting anti-fusarium gene expression in barley" May 23, 2004. Proceedings International Barley Genetics Symposium. Paper No. 157.

* cited by examiner

Figure 1A

ZM-LTP1 promoter

CGGCAAGGCGCTGATTCCGGTAGTGCATATTCGGTGCACATATGATGTACATGAAC
TAACAAAGTTTATAAAAAATTCTAAAAAATCATACATGTTCTTTCCATCATACTCCTAT
TATATACAAAATTTCAAGTTCAAATTTGTTATACTTTAGCTGTGATTAAAAAGAGAATA
TTTTAGTCGATTTTCTAATTTAAATTTGTCAGAATTTTTATTTTTTATTATATCTAAAG
TATAATAAATTTGAACTTGGAATTTTGTATATAATTAGAGTAAGATGAAAAAATATGTA
TGAATTATTTCAGAATTTTTTGTGAACTTTGTTAATTCATGTGCACCATATATAAATCA
AAAGCTCATATTCCGGTTCTAAAACGGCGACCGGTGTTGATTTTCTCAGACGAAAG
CCCCTTCCTCCAATAGTGGTAGGATTGCCTGATCACACGAATACACAGCCAACAAA
CTAGCTAACAGATGGAACAGACCAAACTAATTGCTAATTAACGATAGTGCTGAAGAG
TTATAGCAGCGTTGTGCGTACATAGCACGCACGCTCCTCCCTCCTCCATACCATAG
TAGGCTGGAGCTGCAACACCTGCTGCGCGCCAGACGACGACCCCAAGGAACAACC
TCTCCCTAACCACCATCGTCGTCCATCATCACGCGTCGTTGCTTGTGGCGTTGGTG
CTTTGAAAATCTTGCAAGCAGCTACGTTGAATCGCTATCTCTCTCTCTCGTTCATT
CGTATATACGTGACTACTCAAATCGATTCTTACGCGAATCGATCGGCCAGTGTAGTA
CCGCGTACCGGCGGCCATTACCTAGCTCGCGCAAAGTTCTTCCACCAATCAACGAT
CCACAGTGCACATCGATCGATCGAGATAACCAAGATCCAAGAAACTGAAGCAAGCT
ACTATAGCCAGCTAGCTGGACTCCATAGATCGACGACGACGACCTAGCTGCAAGCA
TCACGACAAGCATTCGCCGTCATCCGCCGACCGCCGGCTATAGCCTATAAGTACCA
CGCGCTCGACGCTCCCCGAGAAAACCACCACGAAAAATGTACGCCTAGCTAGCTC
GGAGCTTGTCCAAGCAGAGCTCTGCACGTACTGAACCTGAACACACAGTAGAGTAG
CGCAACGGATCTCGCCATG

Figure 1B

ZM-LTP1 transcript

Acgcctagctagctcggagcttgtccaagcagagctctgcacgtactgaacctgaacacacagtagagtagcgcaacggatct
cgaaATGGCTGCGAGGCTTGCGCTCCTCATCCTTGCCACGACCTTCCTCCTCTCC
GCCGCCGCGGACGGGGGCAGCACCAACTGCCCGTCGCCGCCAATGACCCCGA
CCCCGACGACGCCACAGCCTCCTCCGTCCGACGGGGGCGGGGGCGGGGGTG
GTAACGGCTCCGCCGGCAGCTGCCCGATCGACGCGCTGAAGCTCGAGGTGTG
CGCGAACGTGCTGAACCTGCTGAGGCTGAACATCGGCGTGCCAGACGACGAG
CAGTGCTGCCCGTTGCTGCAGGGGCTCGCCGACCTCGACGCCGCCGTCTGCCT
CTGCCTCGCCATCAGGGCCAACATTCTCGGCATCGTGCTCAACGTCCCCATCG
ACCTCACCCTCCTGCTCAACTACTGCCACAAGGACCGCGTCGCCAGCTTCACC
TGCCCGGCGTGAtgctgtgcatgcatgcaggcgtgcatgacagtacgtgtcatgcatgtacggagtacatgcgtatttc
tacacacagatcgggacctctatatatatactccatctggacaccgccgtaacgacccatcgataaaatcgcgtgtgctgcatgcg
tattatttgttataaataaaatactgtttccaatttgcgcgtatgccggatgtattgcaatatttggattaggtatgtaattaagtaaacttc
cgtatgcgtgtgtaatggcggatctgtattaaaaaaaagaaaatggcatattatttgccaatctatcgtaaacatcatgtcctgtgaa
at

Figure 1C

ZM-LTP1 terminator

TGCTGTGCATGCATGCAGGCGTGCATGACAGTACGTGTCATGCATGTACGGAGTAC
ATGCGTATTTCTACACACAGATCGGGACCTCTATATATATACTCCATCTGGACACCG
CCGTAACGACCCATCGATAAAATCGCGTGTGCTGCATGCGTATTATTTGTTATAAAT
AAAATACTGTTTCCAATTTGCGCGTATGCCGGATGTATTGCAATATTTGGATTAGGT
ATGTAATTAAGTAAACTTCCGTATGCGTGTGTAATGGCGGATCTGTATTAAAAAAAA
GAAAATGGCATATTATTTGCCAATCTATCGTAAACATCATGTCCTGTGAAATAAATGA
TGCAGCGGTGGATCTAGAAATAGCTTAGGGCTTGTTTGGTTTTCACGGAATCATTG
ACGGAATCGTTGCCTAGAACGATTTCTAGCCGGATTGATTGTCTGATTTATATAAGA
TTTGATCAGCTGCAATGATTCATGATATATT

Figure 2

```
CGGCAAGGCGCTGATTCCGGTAGTGCATATTCGGTGCACATATGATGTACATGAACTAACAAAGTTTATAA
AAAATTCTAAAAAATCATACATGTTCTTTCCATCATACTCCTATTATATACAAAATTTCAAGTTCAAATTT
GTTATACTTTAGCTGTGATTAAAAAGAGAATATTTTAGTCGATTTTCTAATTTAAATTTGTCAGAATTTTT
ATTTTTTTATTATATCTAAAGTATAATAAATTTGAACTTGGAATTTTGTATATAATTAGAGTAAGATGAAA
AAATATGTATGAATTATTTCAGAATTTTTTGTGAACTTTGTTAATTCATGTGCACCATATATAAATCAAAA
GCTCATATTCCGGTTCTAAAACGGCGACCGGTGTTGATTTTCTCAGACGAAAGCCCCTTCCTCCAATAGTG
GTAGGATTGCCTGATCACACGAATACACAGCCAACAAACTAGCTAACAGATGGAACAGACCAAACTAATTG
CTAATTAACGATAGTGCTGAAGAGTTATAGCAGCGTTATGCGTACATAGCACGCACGCTCCTCCCTCCTCC
ATACCATAGTAGGCTGGAGCTGCAACACCTGCTGCGCGCCAGACGACGACCCCAAGGAACAACCTCTCCCT
AACCACCATCGTCGTCCATCATCACGCGTCGTTGCTTGTGGCGTTGGTGCTTTGAAAATCTTGCAAGCAGC
TACGTTGAATCGCTATCTCTCTCTCTCTCGTTCATTCGTATATACGTGACTACTCAAATCGATTCTTACGC
GAATCGATCGGCCAGTGTAGTACCGCGTACCGGCGGCCATTACCTAGCTCGCGCAAAGTTCTTCCACCAAT
CAACGATCCACAGTGCACATCGATCGATCGAGATAACCAAGATCCAAGAAACTGAAGCAAGCTACTATAGC
CAGCTAGCTGGACTCCATAGATCGACGACGACGACCTAGCTGCAAGCATCACGACAAGCATTCGCCGTCAT
CCGCCGACCGCCGGCTATAGCCTATAAGTACCACGCGCTCGACGCTCCCCGAGAAAACCACCACGAAAAAT
GTACGCCTAGCTAGCTCGGAGCTTGTCCAAGCAGAGCTCTGCACGTACTGAACCTGAACACACAGTAGAGT
AGCGCAACGGATCTCGCCATG
```

Figure 3

LTP1 PRO Deletions
    - all deletions are being created in the last 700bp of the promoter region

```
ACCGGTGTTGATTTTCTCAGACGAAAGCCCCTTCCTCCAATAGTGGTAGGATTGCCTGATCACACGAATACACAGCC
AACAAACTAGCTAACAGATGGAACAGACCAAACTAATTGCTAATTAACGATAGTGCTGAAGAGTTATAGCAGCGTTA
TGCGTACATAGCACGCACGCTCCTCCCTCCTCCATACCATAGTAGGCTGGAGCTGCAACACCTGCTGCGCGCCAGAC
GACGACCCCAAGGAACAACCTCTCCCTAACCACCATCGTCGTCCATCATCACGCGTCGTTGCTTGTGGCGTTGGTGC
TTTGAAAATCTTGCAAGCAGCTACGTTGAATCGCTATCTCTCTCTCTCTCGTTCATTCGTATATACGTGACTACTCA
AATCGATTCTTACGCGAATCGATCGGCCAGTGTAGTACCGCGTACCGGCGGCCATTACCTAGCTCGCGCAAAGTTCT
TCCACCAATCAACGATCCACAGTGCACATCGATCGATCGAGATAACCAAGATCCAAGAAACTGAAGCAAGCTACTAT
AGCCAGCTAGCTGGACTCCATAGATCGACGACGACGACCTAGCTGCAAGCATCACGACAAGCATTCGCCGTCATCCG
CCGACCGCCGGCTATAGCCTATAAGTACCACGCGCTCGACGCTCCCCGAGAAAACCACCACGAAAAATGTACGCCTA
GCTAGCTCGGAGCTTGTCCAAGCAGAGCTCTGCACGTACTGAACCTGAACACACAGTAGAGTAGCGCAACGGATCTC
GCCATG
```

Deletion: #1(CCAAAC), #2(AGCTAGCT), #3(CTAGCTGCA), #4(CTCTCTCTCT),
5(CATTCGT), #6(ATCCACAGTGCACA)

5'UTR is in italic font

US 7,897,746 B2

PERICARP-PREFERRED PROMOTER FROM MAIZE LIPID TRANSFER PROTEIN GENE

PARENT CASE TEXT

This application is a continuation of previously filed and application U.S. Ser. No. 11/408,223, filed Apr. 20, 2006, and issued as U.S. Pat. No. 7,550,579 on Jun. 23, 2009, which claims benefit under 35 U.S.C. 119(e) to U.S. Ser. No. 60/676,616, filed Apr. 29, 2005, the contents of which are incorporated herein by reference in their entirety.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of operably linked regulatory elements that are functional within the plant host. Choice of the regulatory element will determine when and where within the organism the heterologous DNA sequence is expressed. Where continuous expression is desired throughout the cells of a plant, and/or throughout development, constitutive promoters are utilized. In contrast, where gene expression in response to a stimulus is desired, inducible promoters are the regulatory element of choice. Where expression in specific tissues or organs are desired, tissue-specific promoters may be used. That is, they may drive expression in specific tissues or organs. Such tissue-specific promoters may be temporally constitutive or inducible. In either case, additional regulatory sequences upstream and/or downstream from a core promoter sequence may be included in expression constructs of transformation vectors to bring about varying levels of expression of heterologous nucleotide sequences in a transgenic plant.

As this field develops and more genes become accessible, a greater need exists for transformed plants with multiple genes. These multiple exogenous genes typically need to be controlled by separate regulatory sequences however. Further, some genes should be regulated constitutively whereas other genes should be expressed at certain developmental stages or locations in the transgenic organism. Accordingly, a variety of regulatory sequences having diverse effects is needed.

Diverse regulatory sequences are also needed as undesirable biochemical interactions can result from using the same regulatory sequence to control more than one gene. For example, transformation with multiple copies of a regulatory element may cause problems, such that expression of one or more genes may be affected.

Expression of heterologous DNA sequences in a plant host is dependent upon the presence of an operably linked promoter that is functional within the plant host. Choice of the promoter sequence will determine when and where within the organism the heterologous DNA sequence is expressed. Thus, where expression is desired in a preferred tissue of a plant, tissue-preferred promoters are utilized. In contrast, where gene expression throughout the cells of a plant is desired, constitutive promoters are the regulatory element of choice. Additional regulatory sequences upstream and/or downstream from the core promoter sequence may be included in expression constructs of transformation vectors to bring about varying levels of tissue-preferred or constitutive expression of heterologous nucleotide sequences in a transgenic plant.

Isolation and characterization of pericarp-preferred promoters and terminators that can serve as regulatory elements for expression of isolated nucleotide sequences of interest in a pericarp-preferred manner are needed for impacting various traits in plants and in use with scorable markers. The inventors have isolated just such a promoter and terminator.

BRIEF DESCRIPTION OF THE FIGURES

FIG. 1A shows the sequence of the 1.2 kb ZM-LTP1 promoter (SEQ ID NO: 1) with the 0.8 version shown up to the shaded area and the 0.6 version shown up to the sequences in italics; FIG. 1B shows the sequences of the ZM-LTP1 transcript (SEQ ID NO: 3) with the open reading frame in all caps; and FIG. 1C shows the terminator region (SEQ ID NO: 2).

FIG. 2 is the LTP1-promoter (SEQ ID NO: 1) showing the location of motifs as described in Table 1, and which also shows the TATA box in bold.

FIG. 3 shows the last 776 bases of LTP1 promoter sequence (bases 382-1157 of SEQ ID NO: 1) with six deletion points, and the correspondence of each to the motifs of Table 1 (deletion 1, bases 637-642 of SEQ ID NO: 1; deletion 2, bases 1076-1083 of SEQ ID NO: 1; deletion 3, bases 1110-1129 of SEQ ID NO: 1; deletion 4, bases 8800-890 of SEQ ID NO: 1; deletion 5, bases 894-900 of SEQ ID NO: 1; and deletion 6, bases 1009-1022 of SEQ ID NO: 1).

DETAILED DESCRIPTION OF THE INVENTION

In accordance with the invention, nucleotide sequences are provided that allow regulation of transcription in pericarp. The sequences of the invention comprise regulatory elements associated with pericarp formation and pericarp tissues. Thus, the compositions of the present invention comprise novel nucleotide sequences for plant regulatory elements natively associated with the nucleotide sequences coding for *Zea mays* lipid transfer protein, herein identified as ZM-LTP1.

In an embodiment, the regulatory element drives transcription in a pericarp-preferred manner, wherein said regulatory element comprises a nucleotide sequence selected from the group consisting of: a) sequences natively associated with, and that regulate expression of DNA coding for maize ZM-LTP1 (*Zea mays* lipid transfer protein 1); b) the nucleotide sequence set forth in either of SEQ ID NO: 1 or 2; or c) a sequence comprising a fragment of the nucleotide sequence set forth in either of SEQ ID NO: 1 or 2.

In another embodiment of the invention the regulatory element comprises bases 530 to 1157 of SEQ ID NO: 1 ("1st truncation"). In a further embodiment, the regulatory element comprises bases 707 to 1157 of SEQ ID NO: 1 ("2nd truncation").

Further embodiments are to expression cassettes, transformation vectors, plants, plant cells and plant pericarp comprising the above nucleotide sequences. The invention is further to methods of using the sequence in plants and plant cells. An embodiment of the invention further comprises the nucleotide sequences described above comprising a detectable marker.

During the reproduction process, angiosperms produce an ovary, which, together with its seed develop into a fruit, that is, a ripened ovary or ovaries, and adjacent parts that may be fused to it. The mature ovary wall is the pericarp and encloses the seeds. Manipulation of pericarp properties, expressing proteins to the pericarp, and expressing markers to the pericarp has numerous uses in the plant industry. A promoter expressing proteins in the pericarp layer, is valuable for a variety of applications in expressing heterologous proteins including controlled expression in pericarp tissue of such proteins. Linking the promoter with cell wall biosynthetic genes to regulate expression of such genes is useful in a wide array of situations.

Such a promoter is also useful to target sequences encoding proteins for disease resistance to the pericarp. Additionally, linking a promoter which preferentially expresses to the pericarp with a marker, and, in particular, a visual marker, is be useful in tracking the expression of a linked gene of interest.

A method for expressing an isolated nucleotide sequence in a plant using the regulatory sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in a pericarp-preferred manner.

Frequently it is desirable to have preferential expression of a DNA sequence in a tissue of an organism. For example, increased resistance of a plant to insect attack might be accomplished by genetic manipulation of the plant's genome to comprise a tissue-specific promoter operably linked to a heterologous insecticide gene such that the insect-deterring substances are specifically expressed in the susceptible plant tissues. Preferential expression of the heterologous nucleotide sequence in the appropriate tissue reduces the drain on the plant's resources that occurs when a constitutive promoter initiates transcription of a heterologous nucleotide sequence throughout the cells of the plant.

Alternatively, it might be desirable to inhibit expression of a native DNA sequence within a plant's tissues to achieve a desired phenotype. In this case, such inhibition might be accomplished with transformation of the plant to comprise a tissue-specific promoter operably linked to an antisense nucleotide sequence, such that tissue-specific expression of the antisense sequence produces an RNA transcript that interferes with translation of the mRNA of the native DNA sequence in a subset of the plant's cells.

Under the regulation of the pericarp-specific regulatory elements will be a sequence of interest, which will provide for modification of the phenotype of the pericarp. Such modification includes modulating the production of an endogenous product, as to amount, relative distribution, or the like, or production of an exogenous expression product to provide for a novel function or product in the pericarp.

Definitions

By "pericarp-preferred" is intended favored expression in the pericarp, the wall of the ovary of a plant, and the like.

By "ovary" is meant the ripened ovary or ovaries, and adjacent parts that may be fused to it.

By "regulatory element" is intended sequences responsible expression of the associated coding sequence including, but not limited to, promoters, terminators, enhancers, introns, and the like.

By "terminator" is intended sequences that are needed for termination of transcription: a regulatory region of DNA that causes RNA polymerase to disassociate from DNA, causing termination of transcription.

By "promoter" is intended a regulatory region of DNA capable of regulating the transcription of a sequence linked thereto. It usually comprises a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate and further include elements which impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein may comprise upstream regulatory elements such as those responsible for tissue and temporal expression of the coding sequence, and may include enhancers, the DNA response element for a transcriptional regulatory protein, ribosomoal binding sites, transcriptional start and stop sequences, translational start and stop sequences, activator sequence and the like.

In the same manner, the promoter elements which enable expression in the desired tissue such as the pericarp can be identified, isolated, and used with other core promoters to confirm pericarp-preferred expression. By core promoter is meant the minimal sequence required to initiate transcription, such as the sequence called the TATA box which is common to promoters in genes encoding proteins. Thus the upstream promoter of ZM-LTP1 can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to drive pericarp-preferred expression retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon. The term "isolated" refers to material, such as a nucleic acid or protein, which is: (1) substantially or essentially free from components which normally accompany or interact with the material as found in its naturally occurring environment or (2) if the material is in its natural environment, the material has been altered by deliberate human intervention to a composition and/or placed at a locus in a cell other than the locus native to the material. Methods for isolation of promoter regions are well known in the art.

The ZM-LTP1 promoter set forth in SEQ ID NO:1 is 1157 nucleotides in length and is set forth in FIG. 1A (SEQ ID NO: 1). The ZM-LTP1 promoter was isolated from the *Zea mays* ZM-LTP1 coding region and the ZM-LTP1 transcript is shown in FIG. 1B, (SEQ ID NO: 3) with the transcription start site underlined, and the terminator region is shown in FIG. 1C (SEQ ID NO: 2). It was isolated based on MPSS (Massively Parallel Signature Sequencing) technology from LYNX™ (see Brenner et al, *Nature Biotechnology* 18:630-634 (2000) expression analysis showing strong expression in 10-40 DAP (days after pollination) maize pericarp. The ZM-LTP1 promoter can address expression problems by providing this pattern of expression.

Motifs of about six or eight bases within the ZM-LTP1 promoter sequence were discovered by searching for sequences of similar size and within 100 bases of the position in which they were located. The following motifs are found in the ZM-LTP1 promoter as represented in Table 1, and corresponding to FIG. 2. FIG. 2 underlines the corresponding bases to the motifs listed below. It also shows the TATA box in bold and not underlined. The reference to "Deletion No." refers to the corresponding deletion made in the LTP1 promoter variant as described below in Example 7 and in FIG. 3.

*sus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa, and sorghum.

Promoter sequences from other plants may be isolated according to well-known techniques based on their sequence homology to the homologous coding region of the coding sequences set forth herein. In these techniques, all or part of the known coding sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Cur-*

TABLE 1

| LTP1 Motif/ Deletion Number | Knowing Reg Element | Name | Description |
| --- | --- | --- | --- |
| CCAACAAAC Deletion No. 1 | AACAAAC | AACACOREOSGLUB1 | Core of AACA motifs found in rice (Oryza sativa) glutelin genes, involved in controlling the endosperm-specific expression. Also associated with GCN4 motif in rice glutelin genes and together confer endosperm-specific enhancement to the truncated-90 CaMV35S promoter (See Wu et al., Plant J., 2000 Aug, 23(3) 415-21). |
| AGCTAGCT Deletion No. 2 | TTCCCCTAGCTAGA TACTTCATT (SEQ ID NO: 13) | Itp1D1, | epidermis preferential element |
| CTAGCTGCA Deletion No. 3 | TTCCCCTAGCTAGA TACTTCATT (SEQ ID NO: 14) | Itp1 D1, | epidermis preferential element |
| CTCTCTCTCT Deletion No. 4 | TTTCTCTCTCTC (SEQ ID NO: 15) | 5UTR Py-rich stretch | cis-acting element conferring high transcription levels |
| CATTCGT Deletion No. 5 | TAAAATACTATCCA TTCGTTAATAGTAA AATACT (SEQ ID NO: 16) | AT-rich sequence | element for maximal elicitor-mediated activation (2copies) |
| ATCCAC Deletion No. 6 | AATCCACA — | GT1-motif — | light responsive element — |
| GTGCACA Deletion No. 6 | | | |

The promoter regions of the invention may be isolated from any plant, including, but not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas como-*

*rent Protocols in Molecular Biology,* Chapter 2, Ausubel, et al., Eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Opsahl-Sorteberg, H-G. et al., "Identification of a 49-bp fragment of the HvLTP2 promoter directing aleruone cell specific expression" *Gene* 341:49-58 (2004). Such variants should retain promoter activity, particularly the ability to drive expression in pericarp or pericarp tissues. Activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.), herein incorporated by reference.

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) *Methods Enzymol.* 155:335-350, and Erlich, ed. (1989) *PCR Technology* (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produces unidirectional nested deletions.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al. (1990) *PCR Protocols, A Guide to Methods and Applications,* eds., Academic Press). Primers used in isolating the promoter of the present invention are shown in SEQ ID NOS: 9, 10, 11, and 12.

The pericarp-preferred regulatory elements disclosed in the present invention, as well as variants and fragments thereof, are useful in the genetic manipulation of any plant when operably linked with an isolated nucleotide sequence of interest whose expression is to be controlled to achieve a desired phenotypic response.

By "operably linked" is intended a functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

In one typical embodiment, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994 herein incorporated in it's entirety by reference.

The regulatory elements of the invention can be operably linked in expression cassettes along with isolated nucleotide sequences of interest for expression in the desired plant, more particularly in the pericarp of the plant. Such an expression cassette is provided with a plurality of restriction sites for insertion of the nucleotide sequence of interest under the transcriptional control of the regulatory elements.

The isolated nucleotides of interest expressed by the regulatory elements of the invention can be used for directing expression of a sequence in the seed or plant. This can be achieved by increasing expression of endogenous or exogenous products in pericarp. Alternatively, the results can be achieved by providing for a reduction of expression of one or more endogenous products, particularly enzymes or cofactors in the pericarp. This down regulation can be achieved through many different approaches known to one skilled in the art, including antisense, cosupression, use of hairpin formations, or others, and discussed infra. Importation or exportation of a cofactor also allows for control of pericarp composition. It is recognized that the regulatory elements may be used with their native or other coding sequences to increase or decrease expression of an operably linked sequence in the transformed plant or seed.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms.

Modifications that affect grain traits include increasing the content of oleic acid, or altering levels of saturated and unsaturated fatty acids. Likewise, the level of pericarp proteins, particularly modified pericarp proteins that improve the nutrient value of the pericarp, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997. Another example is lysine and/or sulfur-rich pericarp protein encoded by the soybean 2S albumin described in WO 9735023 filed Mar. 20, 1996, and the chymotrypsin inhibitor from barley, Williamson et al. (1987) *Eur. J. Biochem.* 165: 99-106.

Agronomic traits in pericarps can be improved by altering expression of genes that: affect the response of pericarp or seed growth and development during environmental stress, Cheikh-N et al (1994) *Plant Physiol.* 106(1):45-51) and genes controlling carbohydrate metabolism to reduce kernel abortion in maize, Zinselmeier et al. (1995) *Plant Physiol.* 107(2): 385-391.

It is recognized that any gene of interest, including the native coding sequence, can be operably linked to the regulatory elements of the invention and expressed in the pericarp.

By way of illustration, without intending to be limiting, are examples of the types of genes which can be used in connection with the regulatory sequences of the invention.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*); McDowell & Woffenden, (2003) *Trends Biotechnol.* 21(4): 178-83 and Toyoda et al., (2002) *Transgenic Res.* 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 91/14778; WO 99/31248; WO 01/12731; WO 99/24581; WO 97/40162 and U.S. application Ser. Nos. 10/032,717; 10/414,637; and 10/606,320.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon,* 40 (11): 1515-1539; Ussuf et al. (2001) *Curr Sci.* 80 (7): 847-853; and Vasconcelos & Oliveira (2004) *Toxicon* 44 (4): 385-403. See also U.S. Pat. No. 5,266,317 to Tomalski et al., who disclose genes encoding insect-specific toxins.

(E) An enzyme responsible for a hyperaccumulation of a monoterpene, a sesquiterpene, a steroid, hydroxycinnamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene, U.S. application Ser. Nos. 10/389,432, 10/692,367, and U.S. Pat. No. 6,563,020.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(H) A hydrophobic moment peptide. See PCT application WO 95/16776 and U.S. Pat. No. 5,580,852 (disclosure of peptide derivatives of Tachyplesin which inhibit fungal plant pathogens) and PCT application WO 95/18855 and U.S. Pat. No. 5,607,914) (teaches synthetic antimicrobial peptides that confer disease resistance).

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum.*

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, *Seventh Int'l Symposium on Molecular Plant-microbe Interactions* (Edinburgh, Scotland, 1994) (enzymatic inactivation in transgenic tobacco via production of single-chain antibody fragments).

(L) A virus-specific antibody. See, for example, Tavladoraki et al., Nature 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., *Current Biology*, 5(2):128-131 (1995), Pieterse & Van Loon (2004) *Curr. Opin. Plant Bio.* 7(4):456-64 and Somssich (2003) *Cell* 113(7):815-6.

(P) Antifungal genes (Cornelissen and Melchers, Pl. Physiol. 101:709-712, (1993) and Parijs et al., *Planta* 183: 258-264, (1991) and Bushnell et al., *Can. J. of Plant Path.* 20(2):137-149 (1998). Also see U.S. application Ser. No. 09/950,933.

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors. See U.S. application Ser. No. 10/947,979.

(S) Defensin genes. See WO03000863 and U.S. application Ser. No. 10/178,213.

(T) Genes conferring resistance to nematodes. See WO 03/033651 and Urwin et. al., *Planta* 204:472-479 (1998), Williamson (1999) *Curr Opin Plant Bio.* 2(4):327-31.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035.

2. Transgenes that Confer Resistance to a Herbicide Such as:

(A) An herbicide that inhibits the growing point or meristem, such as an imidazolinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet.* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627, 061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491, 288; and international publications EP1173580; WO 01/66704; EP1173581 and EP1173582. Glyphosate resistance is also imparted to plants that express a gene that encodes a glyphosate oxido-reductase enzyme as described more fully in U.S. Pat. Nos. 5,776,760 and 5,463,175. In addition glyphosate resistance can be imparted to plants by the over expression of genes encoding glyphosate N-acetyl-transferase. See, for example, U.S. application Ser. Nos. US01/46227; 10/427,692 and 10/427,692. A DNA molecule encoding a mutant aroA gene can be obtained under ATCC accession No. 39256, and the nucleotide sequence of the mutant gene is disclosed in U.S. Pat. No. 4,769,061 to Comai. European Patent Application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903. Exemplary genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet. 246: 419). Other genes that confer resistance to herbicides include: a gene encoding a chimeric protein of rat cytochrome P4507A1 and yeast NADPH-cytochrome P450 oxidoreductase (Shiota et al. (1994) *Plant Physiol.* 106:17), genes for glutathione reductase and superoxide dismutase (Aono et al. (1995) *Plant Cell Physiol* 36:1687, and genes for various phosphotransferases (Datta et al. (1992) *Plant Mol Biol* 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825.

3. Transgenes that Confer or Contribute to an Altered Grain Characteristic, Such as:

(A) Altered fatty acids, for example, by (1) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn), (2) Elevating oleic acid via FAD-2 gene modification and/or decreasing linolenic acid via FAD-3 gene modification (see U.S. Pat. Nos. 6,063,947; 6,323,392; 6,372,965 and WO 93/11245), (3) Altering conjugated linolenic or linoleic acid content, such as in WO 01/12800, (4) Altering LEC1, AGP, Dek1, Superal1, mi1ps, various Ipa genes such as Ipa1, Ipa3, hpt or hggt. For example, see WO 02/42424, WO 98/22604, WO 03/011015, U.S. Pat. Nos. 6,423,886, 6,197,561, 6,825,397, US2003/0079247, US2003/0204870, WO02/057439, WO03/011015 and Rivera-Madrid, R. et. al. *Proc. Natl. Acad. Sci.* 92:5620-5624 (1995).

(B) Altered phosphorus content, for example, by the (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., *Maydica* 35: 383 (1990) and/or by altering inositol kinase activity as in WO 02/059324, US2003/0009011, WO 03/027243, US2003/0079247, WO 99/05298, U.S. Pat. Nos. 6,197, 561, 6,291,224, 6,391,348, WO2002/059324, US2003/0079247, WO98/45448, WO99/55882, WO01/04147.

(C) Altered carbohydrates effected, for example, by altering a gene for an enzyme that affects the branching pattern of starch or a gene altering thioredoxin (See U.S. Pat. No. 6,531, 648). See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus lichenifonnis* alpha-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley alpha-amylase gene), and Fisher et al., *Plant Physiol.* 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US2004/0025203 (UDPGdH), U.S. Pat. No. 6,194,638 (RGP).

4. Genes that Control Male-sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. *Plant Mol. Biol.* 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640.

5. Genes that create a site for site specific DNA integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and WO 99/25821, which are hereby incorporated by reference. Other systems that may be used include the Gin recombinase of phage Mu (Maeser et al., 1991, *Mol Gen Genet.;* 230(1-2):170-6.); Vicki Chandler, *The Maize Handbook* ch. 118 (Springer-Verlag 1994), the Pin recombinase of *E.*

*coli* (Enomoto et al., 1983), and the R/RS system of the pSR1 plasmid (Araki et al., 1992. *J Mol Biol.* 5; 225(1):25-37.

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO2000/060089, WO2001/026459, WO2001/035725, WO2001/034726, WO2001/035727, WO2001/036444, WO2001/036597, WO2001/036598, WO2002/015675, WO2002/017430, WO2002/077185, WO2002/079403, WO2003/013227, WO2003/013228, WO2003/014327, WO2004/031349, WO2004/076638, WO98/09521, and WO99/38977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO02/02776, WO2003/052063, JP2002281975, U.S. Pat. No. 6,084,153, WO0164898, U.S. Pat. Nos. 6,177,275, and 6,107,547 (enhancement of nitrogen utilization and altered nitrogen responsiveness). For ethylene alteration, see US20040128719, US20030166197 and WO2000/32761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), and WO2004/076638 and WO2004/031349 (transcription factors).

Commercial traits in plants can be created through the expression of genes that alter starch or protein for the production of paper, textiles, ethanol, polymers or other materials with industrial uses.

Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering (see Nobrega et. al., *Nature* 431:988-993(04)), homologous recombination, TILLING (Targeting Induced Local Lesions In Genomes), and biosynthetic competition to manipulate, the expression of proteins. Many techniques for gene silencing are well known to one of skill in the art, including but not limited to knock-outs (such as by insertion of a transposable element such as Mu, Vicki Chandler, *The Maize Handbook* ch. 118 (Springer-Verlag 1994) or other genetic elements such as a FRT, Lox or other site specific integration site; RNA interference (Napoli et al. (1990) *Plant Cell* 2:279-289; U.S. Pat. No. 5,034,323, Sharp (1999) *Genes Dev.* 13:139-141, Zamore et al. (2000) *Cell* 101:25-33; and Montgomery et al. (1998) *PNAS USA* 95:15502-15507); virus-induced gene silencing (Burton, et al. (2000) *Plant Cell* 12:691-705, and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525, and Perriman et al. (1993) *Antisense Res. Dev.* 3:253); oligonucleotide mediated targeted modification (e.g., WO 03/076574 and WO 99/25853); zinc-finger targeted molecules (e.g., WO 01/52620; WO 03/048345; and WO 00/42219); and other methods or combinations of the above methods known to those of skill in the art.

Any method of increasing or inhibiting a protein can be used in the present invention. Several examples are outlined in more detail below for illustrative purposes.

The nucleotide sequence operably linked to the regulatory elements disclosed herein can be an antisense sequence for a targeted gene. (See, e.g., Sheehy et al. (1988) *PNAS USA* 85:8805-8809; and U.S. Pat. Nos. 5,107,065; 5,453,566; and 5,759,829). By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant pericarp.

As noted, other potential approaches to impact expression of proteins in the pericarp include traditional co-supression, that is, inhibition of expression of an endogenous gene through the expression of an identical structural gene or gene fragment introduced through transformation (Goring, D. R., Thomson, L., Rothstein, S. J. 1991. *Proc. Natl. Acad. Sci. USA* 88:1770-1774 co-suppression; Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244:230-241)). In one example, co-suppression can be achieved by linking the promoter to a DNA segment such that transcripts of the segment are produced in the sense orientation and where the transcripts have at least 65% sequence identity to transcripts of the endogenous gene of interest, thereby suppressing expression of the endogenous gene in said plant cell. (See, U.S. Pat. No. 5,283,184). The endogenous gene targeted for co-suppression may be a gene encoding any protein that accumulates in the plant species of interest. For example, where the endogenous gene targeted for co-suppression is the 50 kD gamma-zein gene, co-suppression is achieved using an expression cassette comprising the 50 kD gamma-zein gene sequence, or variant or fragment thereof.

Additional methods of co-suppression are known in the art and can be similarly applied to the instant invention. These methods involve the silencing of a targeted gene by spliced hairpin RNA's and similar methods also called RNA interference and promoter silencing (see Smith et al. (2000) *Nature* 407:319-320, Waterhouse and Helliwell (2003)) *Nat. Rev. Genet.* 4:29-38; Waterhouse et al. (1998) *Proc. Natl. Acad. Sci. USA* 95:13959-13964; Chuang and Meyerowitz (2000) *Proc. Natl. Acad. Sci. USA* 97:4985-4990; Stoutjesdijk et al. (2002) *Plant Phystiol.* 129:1723-1731; and Patent Application WO 99/53050; WO 99/49029; WO 99/61631; WO 00/49035 and U.S. Pat. No. 6,506,559.

For mRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

In one embodiment, the polynucleotide to be introduced into the plant comprises an inhibitory sequence that encodes a zinc finger protein that binds to a gene encoding a protein of the invention resulting in reduced expression of the gene. In particular embodiments, the zinc finger protein binds to a regulatory region of a gene of the invention. In other embodiments, the zinc finger protein binds to a messenger RNA encoding a protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355.

The expression cassette may also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source.

The ZM-LTP1 terminator set forth in SEQ ID NO:2 and shown in FIG. 2C is 486 nucleotides in length. The coding region was identified according to the procedure described in Woo et al, *Journal Plant Cell* 13(10), 2297-2317 (2001) incorporated herein by reference. The terminator can be isolated with the primers of SEQ ID NOS: 4 and 5. The terminator, with the appropriate promoter, can provide expression during about 10-40 DAP development. The ZM-LTP1 terminator can be used with the ZM-LTP1 promoter in an expression cassette, or can be used with another appropriate promoter to provide seed-preferred expression of a coding region.

Any convenient termination regions can be used in conjunction with the promoter of the invention, and are available from the Ti-plasmid of *A. tumefaciens,* such as the octopine synthase and nopaline synthase termination regions. See also: Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Natl. Acad. Sci. USA* 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA,* pages 237-256; and maize chlorotic mottle virus leader (MCMV), Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have an expressed product of an isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra).

The transformation vector comprising the regulatory sequences of the present invention operably linked to an isolated nucleotide sequence in an expression cassette, can also contain at least one additional nucleotide sequence for a gene to be cotransformed into the organism. Alternatively, the additional sequence(s) can be provided on another transformation vector.

Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included. For ease of obtaining sufficient quantities of vector, a bacterial origin that allows replication in *E. coli* can be used.

Reporter genes can be included in the transformation vectors. Examples of suitable reporter genes known in the art can be found in, for example: Jefferson et al. (1991) in *Plant Molecular Biology Manual,* ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *Bio Techniques* 19:650-655; and Chiu et al. (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) *Science* 233:478-481; phosphinothricin, DeBlock et al. (1987) *EMBO J.* 6:2513-2518.

Further, when linking a pericarp promoter of the invention with a nucleotide sequence encoding a detectable protein, expression of a linked sequence can be tracked in the pericarp, thereby providing a useful so-called screenable or scorable markers. The expression of the linked protein can be detected without the necessity of destroying tissue. More recently, interest has increased in utilization of screenable or scorable markers. By way of example without limitation, the promoter can be linked with detectable markers including a β-glucuronidase, or uidA gene (GUS), which encodes an enzyme for which various chromogenic substrates are known (Jefferson, R. A. et al., 1986, *Proc. Natl. Acad. Sci. USA* 83:8447-8451); chloramphenicol acetyl transferase; alkaline phosphatase; a R-locus gene, which encodes a product that regulates the production of anthocyanin pigments (red color) in plant tissues (Dellaporta et al., in *Chromosome Structure and Function,* Kluwer Academic Publishers, Appels and Gustafson eds., pp. 263-282 (1988); Ludwig et al. (1990) *Science* 247:449); a p-lactamase gene (Sutcliffe, *Proc. Nat'l. Acad. Sci. U.S.A.* 75:3737 (1978)), which encodes an enzyme for which various chromogenic substrates are known (e.g., PADAC, a chromogenic cephalosporin); a xylE gene (Zukowsky et al., *Proc. Nat'l. Acad. Sci. U.S.A.* 80:1101 (1983)), which encodes a catechol dioxygenase that can convert chromogenic catechols; an α-amylase gene (Ikuta et al., *Biotech.* 8:241 (1990)); a tyrosinase gene (Katz et al., *J. Gen. Microbiol.* 129:2703 (1983)), which encodes an enzyme capable of oxidizing tyrosine to DOPA and dopaquinone, which in turn condenses to form the easily detectable compound melanin a green fluorescent protein (GFP) gene (Sheen et al., *Plant J.* 8(5):777-84 (1995)); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); DS-RED EXPRESS (Matz, M. V. et al (1999) *Nature Biotech.* 17:969-973, Bevis B. J et al. (2002) *Nature Biotech* 20:83-87, Haas, J. et al. (1996) *Curr. Biol.* 6:315-324); *Zoanthus* sp. yellow fluorescent protein (ZsYellow) that has been engineered for brighter fluorescence (Matz et al. (1999) *Nature Biotech.* 17:969-973, available from BD Biosciences Clontech, Palo Alto, Calif., USA, catalog no. K6100-1); and cyan florescent protein (CYP) (Bolte et al. (2004) *J. Cell Science* 117:943-54 and Kato et al. (2002) *Plant Physiol* 129:913-42).

A transformation vector comprising the particular regulatory sequences of the present invention, operably linked to an isolated nucleotide sequence of interest in an expression cassette, can be used to transform any plant. In this manner, genetically modified plants, plant cells, plant tissue, pericarp, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320-334; electroporation, Riggs et al. (1986) *Proc. Natl. Acad. Sci. USA* 83:5602-5606; *Agrobacterium*-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945,050, Tomes et al. (1995) in *Plant Cell, Tissue, and Organ Culture: Fundamental Methods,* ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Bio/Technology* 8:736-740 (rice); Klein et al. (1988) *Proc. Natl. Acad. Sci. USA* 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature* (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues,* ed. G. P. Chapman et al. (Longman, N.Y.), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); D. Halluin et al. (1992) *Plant Cell* 4:1495-1505 (electroporation); Li et al. (1993) *Plant Cell Reports* 12:250-255 and Christou et al. (1995) *Annals of Botany* 75:407-413 (rice); Osjoda et al. (1996) *Nature Biotechnology* 14:745-750 (maize via *Agrobacterium tumefaciens*).

The cells that have been transformed can be grown into plants in accordance with conventional methods. See, for example, McCormick et al. (1986) *Plant Cell Reports* 5:81-84. These plants can then be grown and pollinated with the same transformed strain or different strains. The resulting plant having pericarp-preferred expression of the desired phenotypic characteristic can then be identified. Two or more generations can be grown to ensure that pericarp-preferred expression of the desired phenotypic characteristic is stably maintained and inherited.

The following examples are offered by way of illustration and not by way of limitation.

EXAMPLES

Regulatory regions from maize ZM-LTP1 (*Zea mays* lipid transfer protein 1) were isolated from maize plants and cloned. Maize ZM-LTP1 was selected as a source of pericarp-preferred regulatory elements based on the spatial and temporal expression of its products. The method for their isolation is described below.

Example 1

Prediction of Expression Via Lynx MPSS

Lynx™ gene expression profiling technology was used to identify the maize ZM-LTP1 coding region as a candidate for promoter isolation. Massively parallel signature sequencing (MPSS, see Brenner et al, *Nature Biotechnology* 18:630-634, 2000) indicated expression in various genotypes at about 10

DAP (days after pollination) in pericarp, peaking at about 40 k ppm. Results are summarized in Table 2 below. It was not surprising to find that detectable expression in red pericarp was lower, since this phenotype results from the presence of anthocyanins, known to interfere with RNA isolation. Expression was observed in the red pericarp tissue, but due to the difficulties with RNA isolation associated with this phenotype, the ability to fully measure RNA present with this method is inhibited. MPSS data showed no significant expression of maize ZM-LTP1 in flowering or vegetative tissue.

TABLE 2

| PPM Adj | Tissue | Title |
| --- | --- | --- |
| 0 | ear | Immature ear (5-10 mm), tip |
| 12 | embryo | 21 DAP embryo |
| 3 | embryo | 24 DAP embryo |
| 36 | embryo | 30 DAP embryo |
| 21 | embryo | 35 DAP embryo |
| 16 | embryo | 40 DAP embryo |
| 8 | embryo | 45 DAP embryo |
| 25 | endosperm | 12 DAP endosperm |
| 240 | endosperm | 21 DAP endosperm |
| 32 | endosperm | 30 DAP endosperm |
| 61 | leaf | Leaves, V2 |
| 5001 | pericarp | 15 DAP pericarp |
| 177 | pericarp | 22 DAP pericarp, red, Co63P1-rr |
| 39492 | pericarp | 22 DAP pericarp, white, Co63P1-ww |
| 8476 | pericarp | 27 DAP pericarp |
| 9 | stem - sheath | Corn stem, sheath, V7-8 |

Example 2

Prediction of Expression Pattern Via RT PCR

RT-PCR was performed on maize whole kernels from 1-46 DAP as well as pooled embryo, endosperm, pericarp, leaf, shoot, root, and anther tissue. Results as shown by gel electrophoresis agreed with the MPSS data. The RT-PCR data indicated expression at about 10 DAP up to at least about 40 DAP. Signal was not detected in vegetative and flowering tissue.

Example 3

Isolation of Regulatory Sequences

Using three different LYNX tags (GATCTGTAT-TAAAAAAA, GATCTCGAAATGGCTGC, GATCGG-GACCTCTATAT; SEQ ID NOS: 6, 7, and 8 respectively) and the ESTs containing those tags, a contig sequence was assembled which represented the LTP1 transcript. The promoter sequence was obtained by BLASTing the transcript sequence against a library of maize genes available from Iowa State University (called MAGI). This is a collection of maize sequences from the GSS (Genome Survey Sequence) where the overlapping sequences have been assembled into contigs. MAGI_37138 was the top BLAST hit in the collection. This contig contained a significant region of upstream sequence and downstream sequence. By designing primers on this sequence, three versions of the promoter (varying in length) and one version of the terminator were amplified from B73 genomic DNA using PCR. Additional sequence was added to the end of each primer to create restriction enzyme sites to facilitate cloning. Once amplified, the PCR fragments were sequenced and assembled into expression cassettes using the DS-RED EXPRESS coding region (supra) as the marker gene.

Example 4

Expression Data Using Promoter Sequences

Five promoter::DS-RED EXPRESS::terminator fusion constructs were prepared as set out below. DS-RED EXPRESS is the scorable marker (Matz, M. V. et al 91999) Nature Biotech. 17:969-973, Bevis B. J et al. (2002) Nature Biotech 20:83-87, Haas, J. et al. (1996) Curr. Biol. 6:315-324). The reference to "ubi" indicates a ubiquitin promoter (see, for example, EP 0 342 926B1; U.S. Pat. No. 6,020,109) used as the control, "ZM-LTP1 term" refers to the ZM-LTP1 terminator and "pinII" is the proteinase inhibitor II transcription terminator (An et al, (1989) Plant Cell 1:115-122). All vectors were constructed using standard molecular biology techniques (Sambrook et al., supra).
(a) UBI:UBI INTRON:DS-RED EXPRESS:PINII) (Positive Control)
(b) ZM-LTP1 PRO (0.6):DS-RED EXPRESS:ZM-LTP1 TERM
(c) ZM-LTP1 PRO (0.8):DS-RED EXPRESS: ZM-LTP1 TERM.
(d) ZM-LTP1 (1.2 kb) PRO:DS-RED EXPRESS:ZM-LTP1 TERM.
(e) ZM-LTP1 PRO (1.2 KB):ADH1 INTRON1 (PHI):DS-RED EXPRESS:ZM-LTP1 TERM Successful subcloning was confirmed by restriction analysis. Transformation and expression was confirmed as discussed infra.

Example 5

Transformation of Maize by Particle Bombardment

Preparation of Particles

Sixty mg of 0.6 u BioRad gold particles was weighed and placed in a 2 ml microfuge tube. 1 ml of 100% EtOH was added to the gold particles and sonicated briefly (Branson Sonifier Model 450, 40% output, constant duty cycle), the vortexed on high for 1 minute. The gold particles were pelleted by centrifugation at 10000 rpm (Biofuge) for one minute, and the EtOH was withdrawn. This EtOH wash was repeated two more times. After the last centrifugation, the 100% EtOH was withdrawn and replaced with 1 ml sterile deionized water and briefly sonicated. The solution was then aliquoted into 250 ul aliquots, and 750 ul of sterile deionized water was added to each aliquot.

Preparation of Particle-Plasmid DNA Association 100 ul of the tungsten particle (0.6 u gold particles) solution was briefly sonicated. 10 ul of plasmid DNA (100 ng/ul), 100 μl 2.5 M $CaCl_2$, and 10 μl 0.1 M spermidine was added and vortexed for 10 minutes at a medium speed.

After the association period, the tubes were centrifuged briefly, liquid removed, washed with 500 μl 100% ethanol by sonicating for 3 seconds, and centrifuging for 30 seconds. Again the liquid was removed, and 105 μl of 100% ethanol added to the final tungsten pellet. The associated particles/DNA were briefly sonicated and 10 μl spotted onto the center of each macro-carrier and allowed to dry ~2 minutes before bombardment.

Preparation of Target Kernels

Kernels were grown in the greenhouse until they reached 12 DAP (Days After Pollination). Plants used were of a high oil maize line, which produces ears that pollinate well and have slightly larger kernels than wild-type. Whole kernels were removed from the ear at the pedicel and placed embryo side down on Embryo Sac Culture media (586M) containing MS Salts, MS Vitamins, Thiamin-HCL, Asparagine, BAP, and Sucrose.

Particle Bombardment

To effect particle bombardment of pericarp of kernels, the particle-DNA agglomerates were accelerated using a DuPont PDS-1000 particle acceleration device. The particle-DNA agglomeration was briefly sonicated and 10 µl were deposited on macrocarriers and the ethanol allowed to evaporate. The macrocarrier was accelerated onto a stainless-steel stopping screen by the rupture of a polymer diaphragm (rupture disk). Rupture is effected by pressurized helium. The velocity of particle-DNA acceleration is determined based on the rupture disk breaking pressure. A rupture disk pressure of 1100 psi was used.

The shelf containing the plate with the 12 DAP kernels was placed 5.1 cm below the bottom of the macrocarrier platform (shelf #3). To effect particle bombardment of the kernels, a rupture disk and a macrocarrier with dried particle-DNA agglomerates were installed in the device. The He pressure delivered to the device was adjusted to 200 psi above the rupture disk breaking pressure. A Petri dish with the target kernels was placed into the vacuum chamber and located in the projected path of accelerated particles. A vacuum was created in the chamber, preferably about 28 in Hg. After operation of the device, the vacuum was released and the Petri dish removed.

Bombarded kernels were analyzed for expression of DS-RED EXPRESS 30 hours after bombardment. Ability of the ZM-LTP1 promoter to drive expression in maize pericarp was confirmed by DS-RED EXPRESS detection in the pericarp of bombarded kernels. Strong signal in pericarp was microscopically visualized. DS-RED EXPRESS is visualized using a Xenon light source and the appropriate filters to excite the protein and capture the emitted light. (Excitation: 557 nm, Emission: 579 nm).

Example 6

Transformation and Regeneration of Maize Callus Via *Agrobacterium*

Constructs used were as those set forth supra for microprojectile bombardment, except that the control was not employed in this experiment and the selectable marker for maize-optimized PAT (phosphinothricin acetyl transferase) was also included. Jayne et al., U.S. Pat. No. 6,096,947

Preparation of *Agrobacterium* Suspension:

*Agrobacterium* was streaked out from a −80° frozen aliquot onto a plate containing PHI-L medium and was cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) was added to a concentration of 50 mg/l in sterile ddH2O (stock solution A: K2HPO4 60.0 g/l, NaH2PO4 20.0 g/l, adjust pH to 7.0 w/KOH and autoclaved; stock solution B: NH4Cl 20.0 g/l, MgSO4.7H2O 6.0 g/l, KCl 3.0 g/l, CaCl2 0.20 g/l, FeSO4.7H2O 50.0 mg/l, autoclaved; stock solution C: glucose 5.56 g/l, agar 16.67 g/l (#A-7049, Sigma Chemicals, St. Louis, Mo.) and was autoclaved).

The plate can be stored at 4° C. and used usually for about 1 month. A single colony was picked from the master plate and was streaked onto a plate containing PHI-M medium [yeast extract (Difco) 5.0 g/l; peptone (Difco)10.0 g/l; NaCl 5.0 g/l; agar (Difco) 15.0 g/l; pH 6.8, containing 50 mg/L spectinomycin] and was incubated at 28° C. in the dark for 2 days.

Five ml of either PHI-A, [CHU(N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2, 4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4'-hydroxyacetophenone, Aldrich chemicals) was added to a 14 ml Falcon tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension is adjusted to 0.72 at 550 nm by adding either more *Agrobacterium* or more of the same suspension medium, for an *Agrobacterium* concentration of approximately $0.5 \times 10^9$ cfu/ml to $1 \times 10^9$ cfu/ml. The final *Agrobacterium* suspension was aliquoted into 2 ml microcentrifuge tubes, each containing 1 ml of the suspension. The suspensions were then used as soon as possible.

Embryo Isolation, Infection and Co-cultivation:

About 2 ml of the same medium (here PHI-A or PHI-I) which is used for the *Agrobacterium* suspension was added into a 2 ml microcentrifuge tube. Immature embryos were isolated from a sterilized ear with a sterile spatula (Baxter Scientific Products S1565) and dropped directly into the medium in the tube. A total of about 100 embryos are placed in the tube. The optimal size of the embryos was about 1.0-1.2 mm. The cap was then closed on the tube and the tube vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of *Agrobacterium* suspension was added to the embryos and the tube is vortexed for 30 sec. The tube was allowed to stand for 5 min. in the hood. The suspension of *Agrobacterium* and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2.4-D1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube were transferred to the plate using a sterile spatula. The *Agrobacterium* suspension was drawn off and the embryos placed axis side down on the media. The plate was sealed with Parafilm tape or Pylon Vegetative Combine Tape (product named "E.G.CUT" and is available in 18 mm×50 m sections; Kyowa Ltd., Japan) and was incubated in the dark at 23-25° C. for about 3 days of co-cultivation.

Resting, Selection and Regeneration Steps:

For the resting step, all of the embryos were transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2.4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3-5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000×, Sigma-1511) 1.0 ml/l; thiamine.HCl 0.5 mg/l; 2.4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time.; pH 5.8] putting about 20 embryos onto each plate.

The plates were sealed as described above and incubated in the dark at 28° C. for the first two weeks of selection. The embryos were transferred to fresh selection medium at two-week intervals. The tissue was subcultured by transferring to fresh selection medium for a total of about 2 months. The herbicide-resistant calli are then "bulked up" by growing on the same medium for another two weeks until the diameter of the calli is about 1.5-2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1-3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m-2 sec-1) and 8 hrs. dark until shoots and roots are developed. Each small plantlet was then transferred to a 25×150 mm tube containing PHI-F medium and is grown under the same conditions for approximately another week. The plants were transplanted to pots with soil mixture in a greenhouse. DS-RED EXPRESS events are determined at the callus stage or regenerated plant stage.

Ability of the ZM-LTP1 promoter and truncated variant to drive expression in maize pericarp from 10-40 DAP was confirmed by DS-RED EXPRESS detection in plant pericarp tissue by the procedures outlined supra. In the 1.2 kb version of the promoter, preferred pericarp expression was observed, along with low levels of expression in pollen. In the 0.8 and 0.6 versions of the promoter, pericarp preferred expression was observed, with no expression observed in pollen.

Example 7

Construction of Promoter Variant

Deletion variants are made by removing the promoter sequence at various positions of the promoter region, with the deletions shown in FIG. 3. FIG. 3 also indicates correspondence of each deletion with the motifs of Table 1.

Constructs were prepared as in Example 4, using the truncated variant, linked with the DS-RED EXPRESS marker and LTP1 terminator region. Successful subcloning was confirmed by restriction analysis. Transformation of 12 DAP kernels was carried out using the microprojectile bombardment method set out above. The control ubiquitin promoter demonstrated constitutive expression as evidenced by observation of red fluorescence due to the expression of the linked DS-RED EXPRESS marker.

Three length variations were tested in stable transformation with *agrobacterium:* 1) 1.2 kb (bases 1 to 1157 of SEQ ID NO: 1), 2) 0.8 kb (bases 370 to 1157 of SEQ ID NO: 1), and 3) 0.6 kb (bases 556 to 1157 of SEQ ID NO: 1). All three were capable of driving preferential expression in the Pericarp, however, the two larger fragments also displayed weak expression in pollen.

The Motif deletions were tested transiently using the microprojectile bombardment method as described above. Deletion 1 was created within the 0.8 kb version, while deletions 2-6 were created within the 0.6 kb version. Deletion 3 (bases 1110-1129 of SEQ ID NO: 1), deletion 4 (bases 880-890 of SEQ ID NO: 1) and deletion 6 (bases 1009-1022 of SEQ ID NO: 1) resulted in greatly reduced, to undetectable expression. Deletion 1 (bases 637-642 of SEQ ID NO: 1), deletion 2 (bases 1076-1083 of SEQ ID NO: 1), and deletion 5 (bases 894-900 of SEQ ID NO: 1) had minimal effect on the expression in pericarp.

Although the foregoing invention has been described in some detail by way of illustration and example for purposes of clarity of understanding, it will be obvious that certain changes and modifications may be practiced within the scope of the appended claims. All references cited are incorporate herein by reference.

What is claimed is:

1. An isolated regulatory element comprising a fragment of the nucleotide sequence of SEQ ID NO:1 containing bases 880-890, bases 1009-1022, and bases 1110-1129 of SEQ ID NO:1, wherein said fragment drives transcription in a pericarp-preferred manner or comprising a polynucleotide with at least 90% identity to SEQ ID NO:1, wherein said polynucleotide drives pericarp-preferred expression.

2. An expression cassette comprising the regulatory element of claim 1 and further comprising a nucleic acid molecule operably linked to said regulatory element.

3. A vector comprising the expression cassette of claim 2.

4. A plant comprising a nucleic acid comprising the regulatory element of claim 1 operably linked to a heterologous sequence.

5. A method for expressing a nucleotide sequence in a plant in a pericarp-preferred manner comprising
   (i) transforming a plant cell with the expression cassette of claim 2; and
   (ii) growing the plant cell to produce a plant having said expression cassette such that said nucleic acid molecule is preferentially expressed in the pericarp of said plant.

* * * * *

SEQUENCE LISTING

```
<160> NUMBER OF SEQ ID NOS: 16

<210> SEQ ID NO 1
<211> LENGTH: 1157
<212> TYPE: DNA
<213> ORGANISM: Zea mays
<220> FEATURE:
<221> NAME/KEY: promoter
<222> LOCATION: (1)...(1157)
<223> OTHER INFORMATION: ZM-Ltp1 promoter
<221> NAME/KEY: promoter
<222> LOCATION: (530)...(1157)
```

```
<223> OTHER INFORMATION: .8 truncation
<221> NAME/KEY: promoter
<222> LOCATION: (707)...(1157)
<223> OTHER INFORMATION: .6 truncation

<400> SEQUENCE: 1
ggctatagcc tataagtacc acgcgctcga cgctccccga gaaaaccacc acgaaaaatg      60
tacgcctagc tagctcggag cttgtccaag cagagctctg cacgtactga acctgaacac     120
acagtagagt agcgcaacgg atctcgccat gcggcaaggc gctgattccg gtagtgcata     180
ttcggtgcac atatgatgta catgaactaa caaagtttat aaaaaattct aaaaaatcat     240
acatgttctt tccatcatac tcctattata tacaaaattt caagttcaaa tttgttatac     300
tttagctgtg attaaaaaga gaatatttta gtcgattttc taatttaaat ttgtcagaat     360 ttttatttt ttattatatc taaagtataa taaatttgaa cttggaattt tgtatataat      420
tagagtaaga tgaaaaaata tgtatgaatt atttcagaat tttttgtgaa ctttgttaat     480
tcatgtgcac catatataaa tcaaaagctc atattccggt tctaaaacgg cgaccggtgt     540
tgattttctc agacgaaagc cccttcctcc aatagtggta ggattgcctg atcacacgaa     600
tacacagcca acaaactagc taacagatgg aacagaccaa actaattgct aattaacgat     660
agtgctgaag agttatagca gcgttgtgcg tacatagcac gcacgctcct ccctcctcca     720
taccatagta ggctggagct gcaacacctg ctgcgcgcca gacgacgacc caaggaaca     780 acctctccct aaccaccatc gtcgtccatc atcacgcgtc gttgcttgtg gcgttggtgc     840
tttgaaaatc ttgcaagcag ctacgttgaa tcgctatctc tctctctctc gttcattcgt     900
atatacgtga ctactcaaat cgattcttac gcgaatcgat cggccagtgt agtaccgcgt     960
accggcggcc attacctagc tcgcgcaaag ttcttccacc aatcaacgat ccacagtgca    1020
catcgatcga tcgagataac caagatccaa gaaactgaag caagctacta tagccagcta    1080
gctggactcc atagatcgac gacgacgacc tagctgcaag catcacgaca agcattcgcc    1140
gtcatccgcc gaccgcc                                                   1157

<210> SEQ ID NO 2
<211> LENGTH: 486
<212> TYPE: DNA
<213> ORGANISM: Zea mays
<220> FEATURE:
<221> NAME/KEY: terminator
<222> LOCATION: (1)...(486)
<223> OTHER INFORMATION: ZM-Ltp1 terminator region

<400> SEQUENCE: 2
tgctgtgcat gcatgcaggc gtgcatgaca gtacgtgtca tgcatgtacg gagtacatgc      60
gtatttctac acacagatcg ggacctctat atatatactc catctggaca ccgccgtaac     120
gacccatcga taaaatcgcg tgtgctgcat gcgtattatt tgttataaat aaaatactgt     180
ttccaatttg cgcgtatgcc ggatgtattg caatatttgg attaggtatg taattaagta     240
aacttccgta tgcgtgtgta atggcggatc tgtattaaaa aaaagaaaat ggcatattat     300
ttgccaatct atcgtaaaca tcatgtcctg tgaaataaat gatgcagcgg tggatctaga     360
aatagcttag ggcttgtttg gttttcacgg aatcattgac ggaatcgttg cctagaacga     420
tttctagccg gattgattgt ctgatttata taagatttga tcagctgcaa tgattcatga     480
tatatt                                                                486

<210> SEQ ID NO 3
<211> LENGTH: 765
```

<212> TYPE: DNA
<213> ORGANISM: Zea mays
<220> FEATURE:
<221> NAME/KEY: CDS
<222> LOCATION: (1)...(765)
<223> OTHER INFORMATION: ZM-Ltp1 transcript

<400> SEQUENCE: 3

```
atg gct gcg agg ctt gcg ctc ctc atc ctt gcc acg acc ttc ctc ctc      48
Met Ala Ala Arg Leu Ala Leu Leu Ile Leu Ala Thr Thr Phe Leu Leu
1               5                   10                  15 tcc gcc gcc gcg gac ggg ggc agc acc aac tgc ccg tcg ccg cca atg      96
Ser Ala Ala Ala Asp Gly Gly Ser Thr Asn Cys Pro Ser Pro Pro Met
                20                  25                  30 acc ccg acc ccg acg acg cca cag cct cct ccg tcc gac ggg ggc ggg     144
Thr Pro Thr Pro Thr Thr Pro Gln Pro Pro Pro Ser Asp Gly Gly Gly
            35                  40                  45 ggc ggg ggt ggt aac ggc tcc gcc ggc agc tgc ccg atc gac gcg ctg     192
Gly Gly Gly Gly Asn Gly Ser Ala Gly Ser Cys Pro Ile Asp Ala Leu
50                  55                  60 aag ctc gag gtg tgc gcg aac gtg ctg aac ctg ctg agg ctg aac atc     240
Lys Leu Glu Val Cys Ala Asn Val Leu Asn Leu Leu Arg Leu Asn Ile
65                  70                  75                  80 ggc gtg cca gac gac gag cag tgc tgc ccg ttg ctg cag ggg ctc gcc     288
Gly Val Pro Asp Asp Glu Gln Cys Cys Pro Leu Leu Gln Gly Leu Ala
                85                  90                  95 gac ctc gac gcc gcc gtc tgc ctc tgc ctc gcc atc agg gcc aac att     336
Asp Leu Asp Ala Ala Val Cys Leu Cys Leu Ala Ile Arg Ala Asn Ile
            100                 105                 110 ctc ggc atc gtg ctc aac gtc ccc atc gac ctc acc ctc ctg ctc aac     384
Leu Gly Ile Val Leu Asn Val Pro Ile Asp Leu Thr Leu Leu Leu Asn
        115                 120                 125 tac tgc cac aag gac cgc gtc gcc agc ttc acc tgc ccg gcg tga tgc     432
Tyr Cys His Lys Asp Arg Val Ala Ser Phe Thr Cys Pro Ala *   Cys
130                 135                 140 tgt gca tgc atg cag gcg tgc atg aca gta cgt gtc atg cat gta cgg     480
Cys Ala Cys Met Gln Ala Cys Met Thr Val Arg Val Met His Val Arg
                145                 150                 155 agt aca tgc gta ttt cta cac aca gat cgg gac ctc tat ata tat act     528
Ser Thr Cys Val Phe Leu His Thr Asp Arg Asp Leu Tyr Ile Tyr Thr
160                 165                 170                 175 cca tct gga cac cgc cgt aac gac cca tcg ata aaa tcg cgt gtg ctg     576
Pro Ser Gly His Arg Arg Asn Asp Pro Ser Ile Lys Ser Arg Val Leu
            180                 185                 190 cat gcg tat tat ttg tta taa ata aaa tac tgt ttc caa ttt gcg cgt     624
His Ala Tyr Tyr Leu Leu *   Ile Lys Tyr Cys Phe Gln Phe Ala Arg
        195                 200                 205 atg ccg gat gta ttg caa tat ttg gat tag gta tgt aat taa gta aac     672
Met Pro Asp Val Leu Gln Tyr Leu Asp *   Val Cys Asn *   Val Asn
                210                 215                 220 ttc cgt atg cgt gtg taa tgg cgg atc tgt att aaa aaa aag aaa atg     720
Phe Arg Met Arg Val *   Trp Arg Ile Cys Ile Lys Lys Lys Lys Met
                225                 230                 235 gca tat tat ttg cca atc tat cgt aaa cat cat gtc ctg tga aat         765
Ala Tyr Tyr Leu Pro Ile Tyr Arg Lys His His Val Leu *   Asn
                240                 245
```

<210> SEQ ID NO 4
<211> LENGTH: 38
<212> TYPE: DNA
<213> ORGANISM: Artificial Sequence
<220> FEATURE:
<223> OTHER INFORMATION: ZM-Ltp1 term. primer 838

```
<400> SEQUENCE: 4
ccatgggtta acagatcttg ctgtgcatgc atgcaggc                              38

<210> SEQ ID NO 5
<211> LENGTH: 45
<212> TYPE: DNA
<213> ORGANISM: Artificial Sequence
<220> FEATURE:
<223> OTHER INFORMATION: ZM-Ltp1 term primer 839

<400> SEQUENCE: 5
aagcttgcgg ccgcggtcac caatatatca tgaatcattg cagct                      45

<210> SEQ ID NO 6
<211> LENGTH: 17
<212> TYPE: DNA
<213> ORGANISM: Artificial Sequence
<220> FEATURE:
<223> OTHER INFORMATION: LYNX Tag 1

<400> SEQUENCE: 6
gatctgtatt aaaaaaa                                                     17

<210> SEQ ID NO 7
<211> LENGTH: 17
<212> TYPE: DNA
<213> ORGANISM: Artificial Sequence
<220> FEATURE:
<223> OTHER INFORMATION: LYNX Tag 2

<400> SEQUENCE: 7
gatctcgaaa tggctgc                                                     17

<210> SEQ ID NO 8
<211> LENGTH: 17
<212> TYPE: DNA
<213> ORGANISM: Artificial Sequence
<220> FEATURE:
<223> OTHER INFORMATION: LYNX Tag 3

<400> SEQUENCE: 8
gatcgggacc tctatat                                                     17

<210> SEQ ID NO 9
<211> LENGTH: 28
<212> TYPE: DNA
<213> ORGANISM: Artificial Sequence
<220> FEATURE:
<223> OTHER INFORMATION: ZM-Ltp1 promoter primer 826

<400> SEQUENCE: 9
ggttaccgaa ttccggcaag gcgctgat                                         28

<210> SEQ ID NO 10
<211> LENGTH: 29
<212> TYPE: DNA
<213> ORGANISM: Artificial Sequence
<220> FEATURE:
<223> OTHER INFORMATION: ZM-Ltp1 promoter primer 827

<400> SEQUENCE: 10
ccatggcgag atccgttgcg ctactctac                                        29

<210> SEQ ID NO 11
<211> LENGTH: 29
```

```
<212> TYPE: DNA
<213> ORGANISM: Artificial Sequence
<220> FEATURE:
<223> OTHER INFORMATION: ZM-Ltp1 promoter primer 828

<400> SEQUENCE: 11
ccatggcgag atccgttgcg ctactctac                              29

<210> SEQ ID NO 12
<211> LENGTH: 28
<212> TYPE: DNA
<213> ORGANISM: Artificial Sequence
<220> FEATURE:
<223> OTHER INFORMATION: ZM-Ltp1 promoter primer 829

<400> SEQUENCE: 12
ggttaccgaa ttctcctccc tcctccat                               28

<210> SEQ ID NO 13
<211> LENGTH: 23
<212> TYPE: DNA
<213> ORGANISM: Artificial Sequence
<220> FEATURE:
<223> OTHER INFORMATION: Deletion no. 2

<400> SEQUENCE: 13
ttcccctagc tagatacttc att                                    23

<210> SEQ ID NO 14
<211> LENGTH: 23
<212> TYPE: DNA
<213> ORGANISM: Artificial Sequence
<220> FEATURE:
<223> OTHER INFORMATION: Deletion no. 3

<400> SEQUENCE: 14
ttcccctagc tagatacttc att                                    23

<210> SEQ ID NO 15
<211> LENGTH: 14
<212> TYPE: DNA
<213> ORGANISM: Artificial Sequence
<220> FEATURE:
<223> OTHER INFORMATION: Deletion no. 4

<400> SEQUENCE: 15
tttctctctc tctc                                              14

<210> SEQ ID NO 16
<211> LENGTH: 34
<212> TYPE: DNA
<213> ORGANISM: Artificial Sequence
<220> FEATURE:
<223> OTHER INFORMATION: Deletion no. 5

<400> SEQUENCE: 16
taaaatacta tccattcgtt aatagtaaaa tact                        34
```